(12) United States Patent
Copik et al.

(10) Patent No.: US 10,300,089 B2
(45) Date of Patent: May 28, 2019

(54) METHODS FOR HIGH SCALE THERAPEUTIC PRODUCTION OF MEMORY NK CELLS

(71) Applicant: University of Central Florida Research Foundation, Inc., Orlando, FL (US)

(72) Inventors: Alicja J. Copik, Casselberry, FL (US); Robert Y. Igarashi, Casselberry, FL (US); Jeremiah L. Oyer, Orlando, FL (US); Deborah Altomare, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 15/345,965

(22) Filed: Nov. 8, 2016

(65) Prior Publication Data

US 2018/0125888 A1    May 10, 2018

(51) Int. Cl.
| *A61K 35/17* | (2015.01) |
| *A61K 35/33* | (2015.01) |
| *A61K 38/20* | (2006.01) |
| *A61K 45/06* | (2006.01) |
| *C12N 5/0783* | (2010.01) |

(52) U.S. Cl.
CPC .............. *A61K 35/17* (2013.01); *A61K 35/33* (2013.01); *A61K 38/20* (2013.01); *A61K 38/208* (2013.01); *A61K 38/2086* (2013.01); *A61K 45/06* (2013.01); *C12N 5/0646* (2013.01); *C12N 2501/20* (2013.01); *C12N 2501/2302* (2013.01); *C12N 2501/2312* (2013.01); *C12N 2501/2315* (2013.01); *C12N 2501/2318* (2013.01); *C12N 2501/2321* (2013.01)

(58) Field of Classification Search
CPC ........ A61K 35/17; A61K 35/33; A61K 38/20; A61K 38/2086; A61K 45/06; C12N 2501/20; C12N 2501/2318; C12N 2501/2315; C12N 2501/2312; C12N 2501/2302; C12N 2501/2321
See application file for complete search history.

(56) References Cited

U.S. PATENT DOCUMENTS

| 2013/0059379 A1 | 3/2013 | Schmidt-Wolf |
| 2015/0118207 A1 | 4/2015 | Min et al. |
| 2015/0190471 A1* | 7/2015 | Copik .................. C12N 5/0646 424/85.2 |
| 2015/0258143 A1 | 9/2015 | Malarkannan |

FOREIGN PATENT DOCUMENTS

WO    2016069607 A1    5/2016

OTHER PUBLICATIONS

International Search Report and Written Opinion, issued by the International Searching Authority in Application No. PCT/US17/60614, dated Jan. 23, 2018.

* cited by examiner

*Primary Examiner* — Robert S Landsman
*Assistant Examiner* — Bruce D. Hissong
(74) *Attorney, Agent, or Firm* — Meunier Carlin & Curfman LLC

(57) ABSTRACT

Disclosed are compositions and methods relating to the expansion of memory NK cells.

19 Claims, 1 Drawing Sheet

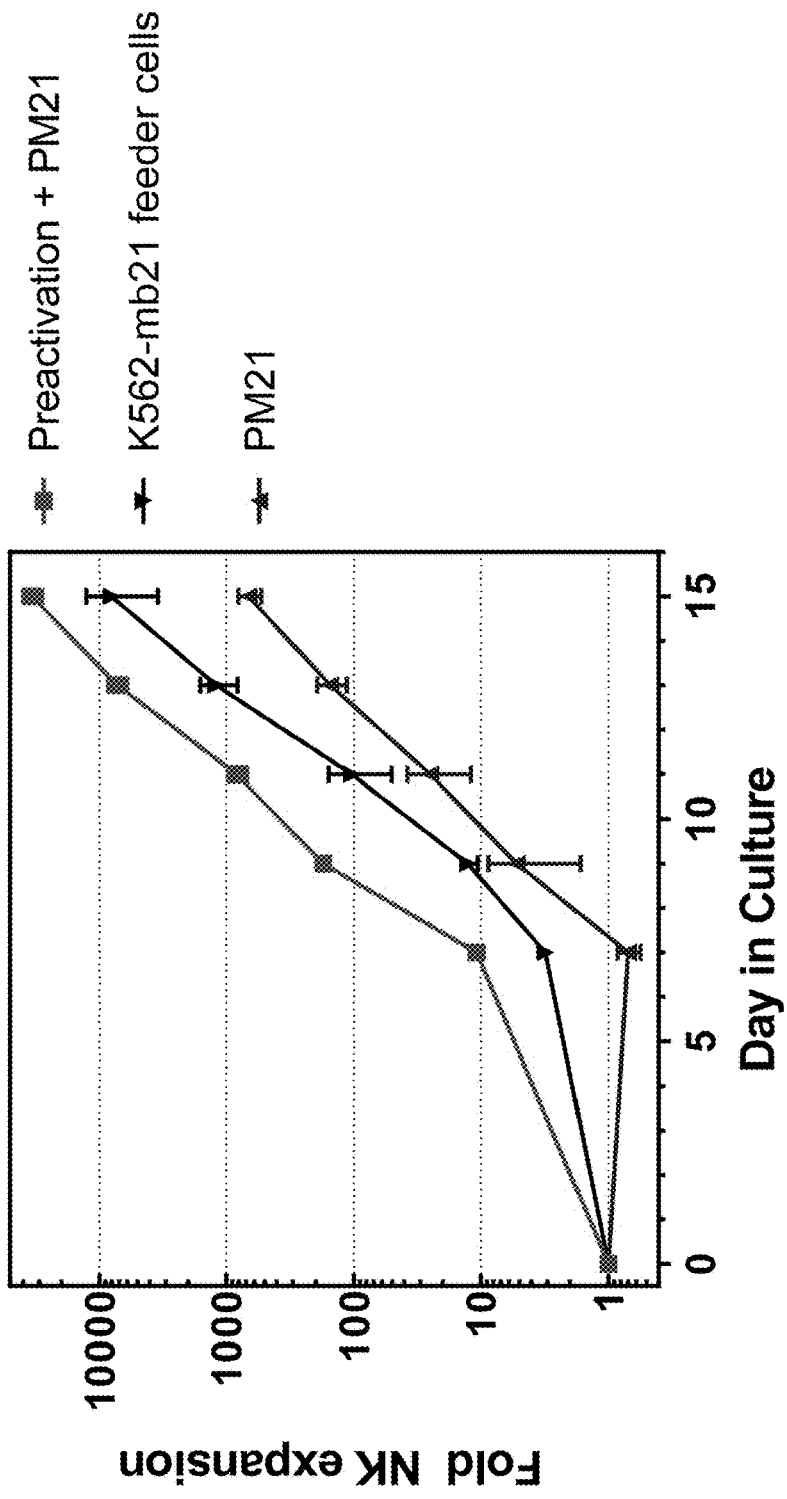

METHODS FOR HIGH SCALE THERAPEUTIC PRODUCTION OF MEMORY NK CELLS

I. BACKGROUND

Hematopoietic stem cell transplantation (HSCT) from genotypically HLA-matched siblings has improved long-term survival in patients with hematologic cancer malignancies and marrow failure syndromes. Every year, more than 10,000 Americans get life-threatening diseases for which the only hope of a cure is a bone marrow transplant from an unrelated donor or cord blood unit. However, more than 70% of patients who could benefit from an allogeneic stem cell transplant do not have a matched sibling donor. These circumstances delay treatment, making it necessary to resort to less than optimal use of a partially mismatched donor, which eventually leads to increased incidence of graft-versus-host disease (GVHD), graft failure, and relapse, all of which dramatically decrease patient survival.

Additional limitations are posed by the duration and the costly financial, mental, and health burdens of the transplant process. Thus, the application of HSCT from an unrelated donor is limited to younger, healthier patients with appropriate socioeconomic support that can endure the process. Further challenges are posed by the high rate of relapse due to the inability to eradicate residual cancer cells. Although HSCT is considered to be curative, cancer relapse rates are staggering. Thus, novel, more targeted immunotherapies are needed that would be more effective, preferably without the need for a matched donor. Donor lymphocyte infusion (DLI), for the treatment of acute myeloid leukemia (AML) relapse after HSCT was introduced in 1990s. This approach consisted of the administration of lymphocytes from the original donor to the AML patient with relapsed disease. Yet, clinical benefits were limited and observed only in a minority of patients with smaller tumor burdens, and T cell mediated GVHD often further worsened the outcomes.

A significant portion of donor lymphocyte infusion mediated graft-versus-tumor (GVT) effect may be due to natural killer (NK) cells. The infusion of NK cells isolated from donor blood could produce beneficial GVT effects without causing GVHD. Preclinical and clinical data has shown effectiveness of NK cell infusions leading toward complete remission without any GVHD. Thus, NK cell infusion, in combination with autologous transplantation, or as a stand-alone treatment, offers an innovative, and potentially very effective, alternative for those patients who do not have a matched donor, experience relapse, or do not qualify for transplant. However, these NK cell treatments create demand for NK cell expansion sufficient in number to provide therapeutic treatment. Accordingly, there is a great need for new and improved methodologies aimed at increasing memory NK cell numbers.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

II. SUMMARY

The present application generally relates to compositions and methods comprising memory natural killer (NK) cells. More particularly, the application relates to the in vivo, ex vivo, or in vitro stimulation and expansion of memory natural killer (NK) cells, which are capable of attacking and killing cancer cells, virally infected cells and certain immune cells.

Disclosed herein are methods for increasing the number of memory NK cells comprising a) preactivating NK cells by contacting at least one NK cell with at least one or more stimulatory cytokines; b) expanding the preactivated NK cells of step a) by contacting said cells with a vesicle comprising an NK cell effector agent (for example, contacting with PM21 particles, EX21 exosomes, or FC21 feeder cells). In some aspect are methods for increasing the number of memory NK cells further comprising washing after the preactivation step a) and/or the expansion step b) and/or resting the memory NK cells after the expansion step b).

In one aspect disclosed herein are methods for increasing the number of memory NK cells wherein the NK cells for use in the disclosed methods are obtained from an unselected population of peripheral blood mononuclear cells.

Also disclosed are methods of any preceding aspect wherein the at least one or more stimulatory cytokines are selected from the group consisting of IL-12, IL-15, and IL-18. In one aspect, the methods can comprise contacting the NK cells with 3 stimulatory cytokines.

Also disclosed are methods of any preceding aspect wherein the NK cells are contacted with the IL-12, IL-15, or IL-18 in vitro, in vivo, or ex vivo.

Also disclosed are methods of any preceding aspect wherein the NK cells are contacted with the one or more stimulatory cytokines for 1, 2, 3, 4, 5, 6, 7, 8, 9, 10, 11, 12, 13, 14, 15, 16, 17, 18, 19, 20, 21, 22, 23, 24, 36, 48, 60, or 72 hours.

Also disclosed are methods of any preceding aspect further comprising contacting the NK cell with a cytokine selected from the group consisting of 4-1BBL, IL-2, IL-21, MICA/B, ULBP2, ICAM-1, 2B4, BCM1/SLAMF2, CD155, CD112, CCR7, DAP12, and DAP10.

In one aspect, disclosed herein are methods wherein the PM21 particles, EX21 exosomes, or FC21 feeder cells comprise one or more stimulatory peptides coupled to a membrane-inserting peptide.

Also disclosed are methods of any preceding aspect wherein membrane-inserting cytokine comprises a fused peptide that is capable of membrane insertion, with affinity for a lipid bilayer, and wherein said fused peptide comprises a segment of IG4, CD4, or a combination thereof.

Also disclosed are methods of any preceding aspect wherein the membrane-inserting peptide comprises human Fc, GPI, trans-membrane T-cell receptor, or pHLIP.

Also disclosed are methods of any preceding aspect wherein the one or more stimulatory peptides are selected from the group consisting of 4-1BBL, IL-2, IL-12, IL-18, IL-21, MICA/B, ULBP2, ICAM-1, 2B4, BCM1/SLAMF2, CD155, CD112, CCR7, DAP12, and DAP10.

Also disclosed are methods of any preceding aspect wherein the one or more stimulatory cytokines coupled to a membrane-inserting peptide is a fusion protein encoded by recombinant DNA.

Also disclosed are methods of any preceding aspect wherein the NK cells are contacted with the PM21 particles, EX21 exosomes, or FC21 feeder cells in vitro, in vivo, or ex vivo.

Also disclosed are methods of any preceding aspect wherein the NK cells of step a) are contacted with PM21 particles, EX21 exosomes, or FC21 feeder cells for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days.

In one aspect, disclosed herein are methods wherein the cells are memory NK cells rested for at least 1, 2, 3, 4, or 5 days.

In one aspect, disclosed herein are kits for increasing the number of memory NK cells comprising one or more cytokine and one or more vesicle comprising an NK cell effector agent.

Also disclosed are kits of any preceding aspect, wherein the one or more cytokines is selected from the group consisting of IL-12, IL-15, and IL-18.

Also disclosed are kits of any preceding aspect, wherein the one or more vesicles comprising an NK cell effector agent is a PM21 particle, EX21 exosome, or FC21 feeder cell.

Also disclosed are kits of any preceding aspect, wherein the NK cell effector agent is selected from the group consisting of -1BBL, IL-2, IL-15, IL-21, MICA/B, ULBP2, ICAM-1, 2B4, BCM1/SLAMF2, CD155, CD112, CCR7, DAP12, and DAP10

III. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows increased memory NK cell expansion following contact with PM21 particles, K562-mb21 feeder cells (FC21 cells), and preactivation with IL12, IL15, and IL18 followed by contact with PM21 particles.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. Definitions

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. Method of Expanding Memory NK Cells

Human NK cells are a subset of peripheral blood lymphocytes defined by the expression of CD56 or CD16 and the absence of T cell receptor (CD3). NK cells sense and kill target cells that lack major histocompatibility complex (MHC)-class I molecules. NK cell activating receptors include, among others, the natural cytotoxicity receptors (NKp30, NKp44 and NKp46), and lectin-like receptors NKG2D and DNAM-1. Their ligands are expressed on stressed, transformed, or infected cells but not on normal cells, making normal cells resistant to NK cell killing. NK cell activation is negatively regulated via inhibitory receptors, such as killer immunoglobin (Ig)-like receptors (KIRs), NKG2A/CD94, and leukocyte Ig-like receptor-1 (LIR-1). Engagement of one inhibitory receptor may be sufficient to prevent target lysis. Hence NK cells efficiently target cells that express many stress-induced ligands, and few MHC class I ligands.

Infusions of NK cells are a treatment option for patients with cancers susceptible to NK cell lysis, including blood cancers (such as acute myeloid leukemia or multiple myeloma) and several solid tumors (e.g. brain tumor, Ewing sarcoma and rhabdomyosarcoma). Increased numbers of functional NK cells can also significantly enhance the efficacy of therapeutic antibodies used in treatment of several cancers, including lymphomas, colorectal cancer, lung cancer, and breast cancer, among others. These types of personalized treatments are, however, very costly, with a typical antibody-containing regimen costing tens of thousands of dollars. Furthermore, the expected efficacy of existing methods is often not achieved due to the lack of immune cell engagement in immune compromised cancer patients.

To be effective as a treatment method, it is desirable to achieve a degree of NK cell expansion that reaches an effective therapeutic dose. However, previous studies show that NK cell expansion was limited to several divisions and the cells achieved senescence and stopped proliferating, coinciding with the observation of telomere shortening. While these methods allow for efficient in vitro NK cell expansion, the need for live feeder cells makes the methodology difficult to transfer to clinical settings that do not have large GMP facility and capability. Also, NK cells that are infused into the patient will likely stop dividing due to the lack of continued stimulation by the feeders. Furthermore, there is still a lack of information about the ability of in vitro cultured NK cells to function as intended when re-infused into a patient. Currently IL-2 administration is the only FDA approved method of expansion of NK cells in vivo. However, the intensive conditioning regimen required for lymphodepletion and the high doses of IL-2 used in this study resulted in significant toxicity and prolonged hospitalization, and in many cases, low in vivo expansion on NK cells. Moreover, systemic administration of IL-2 leads to proliferation of regulatory T cells that suppress the numbers and function of NK cells, thereby limiting their persistence and efficiency in the patient. Thus, alternative approaches for in vivo or ex vivo expansion of NK cells are needed. IL-15 is currently being tested in a Phase I clinical trial as an alternative approach to IL-2 administration but based on preclinical findings it is still expected to have significant toxicity if administered systematically. Thus, both methods carry significant toxicities to patients and also induce proliferation of T-cells including regulatory T-cells leading to short persistence (on average less than 21 days) of NK cells.

As noted above, the efficacy of NK cell immunotherapy is dependent on the dose of NK cells administered to the patient or reached after infusion through in vivo expansion. Currently available techniques are limited by their inability to achieve the level of NK cell expansion required to achieve a therapeutic effect in a patient. The lack of a simpler clinical expansion protocol is a major barrier to the progress and wide dissemination of NK cell-based immunotherapy. Current ex vivo expansion protocols use a combination of high dose cytokines with activating ligands expressed on leukemia-derived feeder/stimulator cell lines, posing a significant disadvantages for transfer to clinical settings in most centers and are not amenable for direct in vivo expansion. The use of particle technology, including exosomes, described herein eliminates the need for stimulator cells, thus simplifying the methodology and allowing direct and selective in vivo expansion. Accordingly, and in one aspect, disclosed herein are methods for increasing the number of memory NK cells comprising a) preactivating NK cells by contacting at least one NK cell with one or more stimulatory cytokines; and b) expanding the preactivated NK cells of step a) by contacting said cells with one or more vesicles comprising an NK cell effector agent.

The disclosed methods accomplish preactivation of NK cells by contacting at least on NK cell with at least one or more stimulatory cytokines (for example IL-12, IL-15, and/or IL-18). Thus, in one aspect, disclosed herein are methods of increasing the number of memory NK cells comprising preactivating NK cells by contacting one or more NK cells with one or more stimulatory cytokines is selected from the group comprising IL-12, IL-15, and/or IL-18, or any combination thereof, including contacting one or more NK cells with 2 or 3 stimulatory cytokines. For example, specifically disclosed herein are methods wherein the preactivation step comprises contact NK cells with IL-12; IL-15, IL-18, IL-12 and IL-15; IL-12 and IL-18; IL-15 and IL-18; or IL-12, IL-15, and IL-18. In one aspect, the disclosed methods of increasing the number of NK cells can further comprise contacting the NK cell with one or more cytokines selected from the group consisting of 4-1BBL, IL-2, IL-21, MICA/B, ULBP2, ICAM-1, 2B4, BCM1/SLAMF2, CD155, CD112, CCR7, DAP12, and/or DAP10.

It is understood and herein contemplated that the duration of preactivation (i.e., the duration of contact between the NK cells and the stimulatory cytokines (e.g., IL-12, IL-15, and/or IL-18) can be for any length of time necessary to achieve the desired preactivation of NK cells. For example, the contact can be as little as 1 minute or as much as 7 days (for example, culturing the NK cells in the presence of IL-12, IL-15, and/or IL-18 for 7 days). In one aspect, disclosed herein are methods of increasing the number of memory NK cells comprising preactivating NK cells by contacting one or more NK cells with IL-12, IL-15, and/or IL-18 for 5, 6, 7, 8, 9, 10, 11, 12, 13, 14, 15, 16, 17, 18, 19, 20, 21, 22, 23, 24, 36, or 48 hours. It is understood and herein contemplated that the half-life of a cytokine in culture may be less than the desired contact time. Accordingly, disclosed herein are methods wherein one or more NK cells are contacted with IL-12, IL-15, and/or IL-18 every 1, 2, 3, 4, 5, 6, 7, 8, 9, 10, 11, or 12 hours within a contact period (for example, every 1, 2, 3, 4, 5, 6, 7, 8, 9, 10, 11, or 12 in a 24 hour contact period).

Through the use of plasma membrane (PM) particles, exosomes (EX), or feeder cells (FC) comprising one or more NK cell effector agents (i.e., stimulatory peptides, cytokines, and/or adhesion molecules) to contact and activate and/or expand NK cells many hurdles associated with cytokine toxicity are overcome. Examples of NK cell activating agents and stimulatory peptides include, but are not limited to, 41BBL, IL-2, IL-12, IL-21, IL-18, MICA, LFA-1, 2B4, BCM/SLAMF2, CCR7 and/or other homing receptors. Examples of cytokines include, but are not limited to, IL-2, IL-12, IL-21, and IL-18. Examples of adhesion molecules include, but are not limited to LFA-1, MICA, BCM/SLAMF2. For example, a plasma membrane (PM) particle, Feeder cells (FC), or exosomes (EX) prepared from feeder cells expressing membrane bound IL-21 (FC21 cells, PM21 particles, and EX21 exosomes, respectively). The membrane bound IL-21 expressing FC21 cells, PM21 particles, and EX21 exosomes can further comprise additional one or more activating agents, stimulatory peptides, cytokines, and/or adhesion molecules including, but not limited to 41BBL, IL-2, IL-12, IL-15, IL-18, MICA, LFA-1, 2B4, BCM/SLAMF2, CCR7 (for example, PM21 particle, EX21 exosome, or FC cell expressing 41BBL and membrane bound interleukin-21). Accordingly, in one aspect, disclosed herein are method for increasing the number of memory NK cells comprising a) preactivating NK cells by contacting at least one NK cell with at least one or more stimulatory cytokines; and b) expanding the preactivated NK cells of step a) by contacting said cells with at least one vesicle comprising an NK cell effector agent; wherein the NK cell effector agent comprising vesicle is any combination of one or more of PM21 particle, EX21 particle, and/or FC21 feeder cells. For example, disclosed herein are methods of increasing memory NK cell numbers comprising, amongst other steps, expanding the preactivated NK cells of step a) by contacting said cells with at least one vesicle comprising an NK cell effector agent wherein the NK cell effector agent comprising vesicle comprises PM21 particles; EX21 exosomes; FC21 feeder cells; PM21 particles and EX21 exosomes; PM21 particles and FC21 feeder cells; EX21 exosomes and FC21 feeder cells; or PM21 particles, EX21 exosomes, and FC21 feeder cells.

In some aspects, effector agents of the PM21 particles, EX21 exosomes, or FC21 feeder cells comprise one or more stimulatory peptides coupled to a membrane-inserting peptide (for example, Fc, GPI, trans-membrane T-cell receptor, or pHLIP). A membrane-inserting peptide may be a molecule that promotes insertion into a membrane. Membrane-inserting peptides may comprise segments of CD4 or an IgG with affinity for a lipid bilayer. In addition, alternative membrane-inserting peptides may comprise human Fc, GPI, trans-membrane T-cell receptor, or pHLIP. The membrane self-inserting peptide may be any peptide known to insert into a cell membrane. Depending on the use of the membrane self-inserting peptide conjugate, certain membrane self-inserting peptides can be better choices than others. One of skill in the art would understand what membrane self-inserting peptide is ideal under different circumstances. For example, for in vivo use, pHLIP membrane self-inserting peptide may be suitable. pHLIP membrane self-inserting peptides insert into the membrane only under conditions of low pH. Therefore, pHLIP conjugates will not insert into cell membranes under normal physiological conditions. However, upon injection into a tumor environment, the pHLIP conjugate can insert into the cell membrane of tumor cells because the tumor environment is more acidic than normal physiological conditions. This insertion into the tumor environment allows for activation of NK cells in the area of the tumor. Using pHLIP thus prevents unwanted insertion into random cell membranes.

Membrane-inserting peptides may be coupled to one or more stimulatory peptides in a variety of ways and techniques for coupling peptides are well known in the art. A membrane-inserting peptide coupled to a stimulatory peptide can also be referred to as a membrane-inserting peptide conjugate. In some aspects, the one or more stimulatory peptides coupled to a membrane-inserting peptide may comprise a fusion protein encoded by recombinant DNA and such fusion-proteins may be produced in bacterial cells. In certain embodiments, fusion proteins may consist of one or more stimulatory peptides conjugated or coupled to a lipophilic molecule such as a hydrophobic peptide, GPI, or human Fc for anchoring into liposomes or cellular membranes. cDNA vectors for these fusion proteins may be ligated into an expression plasmid, which allows expression in bacterial (E. coli), insect, or mammalian cells. In certain embodiments, cDNA vectors may be FLAG- or HIS-tagged. Bacterial cells may be transfected using standard CaCl transfection methods, such as that described in Sambrook et al., Molecular Cloning: A Laboratory Manual. 2nd ed. Cold Spring Harbor Laboratory Press (1989). Bacterial cells may also be cultured in LB media and cells can be harvested and lysed using a French Press. Proteins of interest can be purified from lysates by affinity chromatography. Palmitate-conjugated protein A and purified Fc fusion proteins can be conjugated as described in the literature by mixing 1:2 (w/w) at 4 degrees C. The conjugates may then be directly injected intratumorally or may be incorporated into liposomes.

Types of coupling and methods for coupling are known to those skilled in the art. As used herein, term "couple" refers to the membrane self-inserting peptide being conjugated, connected, or otherwise linked to another molecular entity such as a peptide or protein. For example, membrane-inserting peptides coupled to stimulatory peptides can be fusion proteins wherein the membrane-inserting peptide is coupled to another protein via a disulfide bond. Coupling or conjugating may mean that there is a chemical linkage between the membrane self-inserting peptide and the NK cell effector agent.

In some aspects, one or more stimulatory peptides may be coupled to membrane self-inserting peptides or GPI anchors for in situ self-assembly. For example, 41-BBL and IL-21 may be coupled to a pHLIP peptide which inserts itself into cellular membranes under acidic conditions, thereby allowing the anchoring of the stimulatory ligands into cells in the proximity of tumor. The stimulatory peptides 41BBL, IL-2, IL-12, IL-21, BCM/SLAMF2, CCR7 and/or other homing receptors may be produced in bacterial cells or purchased from commercially available sources and cDNA vectors for these proteins may optionally be ligated into pTriEX expression plasmid which allows expression in bacterial (E. coli), insect, or mammalian cells. The cDNA vector may code for expression of FLAG- or HIS-tag. Bacterial cells can be transfected using standard CaCl transfection methods and may be cultured on LB media. Cells can be harvested and lysed using a French press and proteins of interest may then be purified from lysates by affinity chromatography.

In some embodiments, pHLIP may be prepared by solid-phase peptide synthesis using 9-fluorenylmethyloxycarbonyl chemistry and the product may be purified on a C18 column by reverse-phase chromatography. pHLIP may then be conjugated to stimulatory human protein ligands by incubating with a crosslinker, such as benzophenone-4-iodoacetamide. After several washes, the conjugated pHLIP protein may be resuspended in media (saline, for example) and injected intratumorally or intravenously. Based on evidence from prior literature and presented in experimental results, interaction of NK cells with stimulatory ligands such as IL-21 and 41-BBL on the surface of such modified tumor cells may stimulate in situ NK cell expansion and trigger their cytotoxic response toward a tumor. This type of stimulatory approach can be used for treatments of solid tumors such as ovarian cancer where NK stimulatory ligands that insert in situ into tumor cells under acidic pH can be injected into intraperitoneal space of patients with low dose IL-2 alone or together with NK cells. There is strong evidence that cytotoxic lymphocytes that express high levels of FCγIII R (CD16) such as NK cells are crucial for the efficacy of cancer therapy with therapeutic antibodies. Thus, this approach can also be used in combination with therapeutic antibodies.

It is understood and herein contemplated that the duration of contact between the preactivated NK cells (i.e., NK cells contacted with a cytokine such as IL-12, IL-15, and/pr IL-18) and the NK cell effector agent comprising vesicle (i.e., PM21 particles, EX21 exosomes, and/or FC21 feeder cells) can be for any length of time necessary to achieve the desired expansion of memory NK cells. For example, the contact can be as little as 1 minute or as much as 60 days (for example, culturing the NK cells in the presence of PM21 particles, EX21 exosomes, and/or FC21 feeder cells for 7 days). In one aspect, the contact between the preactivated NK cells and the NK cell effector agent comprising vesicle can be between about 6 days and about 60 day, more preferably the contact can be between about 6 days and about 40 days. Also disclosed herein are methods of increasing the number of memory NK cells comprising contacting the preactivated NK cells with PM21 particles, EX21 exosomes, and/or FC21 feeder cells for 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 days. It is understood and herein contemplated that in some instances, multiple contact of the preactivated NK cells with PM21 particles, EX21 exosomes, and/or FC21 feeder cells may be desired and can be employed. For example, the preactivated NK cells can be contacted with the PM21 particles, EX21 exosomes, and/or FC21 feeder cells once every 1, 2, 3, 4, 5, 6, 7, 8, 9, 10, 11, 12, 18, 24 hrs, 2, 3, 4, 5, 6, 7, 8, 9, 0, 10, 11, 12, 13, 14, 15, 16, 17, 18, 19, 20, or 21 days. Accordingly, in one aspect, disclosed herein are methods of increasing the number of memory NK cells comprising contacting the preactivated NK cells with PM21 particles, EX21 exosomes, and/or FC21 feeder cells more than one time, wherein the contact occurs every 1, 2, 3, 4, 5, 6, 7, 8, 9, 10, 11, 12, 18, 24 hrs, 2, 3, 4, 5, 6, 7, 8, 9, 0, 10, 11, 12, 13, 14, 15, 16, 17, 18, 19, 20, or 21 days.

In one aspect, the plasma membrane particles, feeder cells, or exosomes can be purified from feeder cells that stimulate NK cell. NK cell stimulating feeder cells for use in the claimed invention, for use in making the plasma membrane particles or exosomes, disclosed herein can be either irradiated autologous or allogeneic peripheral blood mononuclear cells (PBMCs) or nonirradiated autologous PBMCs, RPMI8866, HFWT, K562, K562 cells transfected with membrane bound IL-15 and 41BBL, K562 cells transfected with membrane bound IL-21 and 41BBL, or EBV-LCL. In some aspects, the NK cell feeder cells can be K562 cells transfected with membrane bound IL-21 and 41BBL or K562 cells transfected with membrane bound IL-15 and 41BBL.

It is understood and herein contemplated that the use of a particular stimulatory cytokine in the preactivation step has no bearing on the NK cell effector agent comprising vesicle used for expanding the preactivated NK cells. Thus, any combination of cytokines and vesicles can be used in the disclosed methods. For example, specifically disclosed herein are methods for increasing the number of memory NK cells comprising a) preactivating NK cells by contacting at least one NK cell with at least one or more stimulatory cytokines; and b) expanding the preactivated NK cells of step a) by contacting said cells with one or more vesicles comprising an NK cell effector agent (for example, contacting with PM21 particles, EX21 exosomes, or FC21 feeder cells); wherein the one or more stimulatory cytokines is IL-12, IL-15, and/or IL-18 and the one or more vesicles are PM21 particles, EX21 exosomes, and/or FC21 feeder cells. For example, disclosed herein are methods comprising IL-12 and PM21 particles; IL-15 and PM21 particles; IL-18 and PM21 particles; IL-12 and EX21 exosomes, IL-15 and EX21 exosomes; IL-18 and EX21 exosomes; IL-12 and FC21 feeder cells; IL-15 and FC21 feeder cells; IL-18 and FC21 feeder cells; IL-12, IL15, and PM21 particles; IL-12, IL-18, and PM21 particles; IL-15, IL-18, and PM21 particles; IL-12, IL-15, IL-18, and PM21 particles; IL-12, IL15, and EX21 exosomes; IL-12, IL-18, and EX21 exosomes; IL-15, IL-18, and EX21 exosomes; IL-12, IL-15, IL-18, and EX21 exosomes; IL-12, IL15, and FC21 feeder cells; IL-12, IL-18, and FC21 feeder cells; IL-15, IL-18, and FC21 feeder cells; IL-12, IL-15, IL-18, and FC21 feeder cells; IL-12, EX21 exosomes, and PM21 particles; IL-15, EX21 exosomes, and PM21 particles; IL-18, EX21 exosomes, and PM21 particles; IL-12, FC21 feeder cells, and PM21 particles; IL-15, FC21 feeder cells, and PM21 particles; IL-18, FC21 feeder cells, and PM21 particles; IL-12, FC21 feeder cells, and EX21 exosomes; IL-15, FC21 feeder cells, and EX21 exosomes; IL-18, FC21 feeder cells, and EX21 exosomes; IL-12, FC21 feeder cells, PM21 particles, and EX21 exosomes; IL-15, FC21 feeder cells, PM21 particles, and EX21 exosomes; IL-18, FC21 feeder cells, PM21 particles, and EX21 exosomes; IL-12, IL15, EX21 exosomes, and PM21 particles; IL-12, IL-18, EX21 exosomes, and PM21 particles; IL-15, IL-18, EX21 exosomes, and PM21 particles; IL-12, IL-15, IL-18, EX21 exosomes, and PM21 particles; IL-12, IL15, FC21 feeder cells, and PM21 particles; IL-12, IL-18, FC21 feeder cells, and PM21 particles; IL-15, IL-18, FC21 feeder cells, and PM21 particles; IL-12, IL-15, IL-18, FC21 feeder cells, and PM21 particles; IL-12, IL15, EX21 exosomes, and FC21 feeder cells; IL-12, IL-18, EX21 exosomes, and FC21 feeder cells; IL-15, IL-18, EX21 exosomes, and FC21 feeder cells; IL-12, IL-15, IL-18, EX21 exosomes, and FC21 feeder cells; IL-12, EX21 exosomes, FC21 feeder cells, and PM21 particles; IL-15, EX21 exosomes, FC21 feeder cells, and PM21 particles; IL-18, EX21 exosomes, FC21 feeder cells, and PM21 particles; IL-12, IL15, EX21 exosomes, FC21 feeder cells, and PM21 particles; IL-12, IL-18, EX21 exosomes, FC21 feeder cells, and PM21 particles; IL-15, IL-18, EX21 exosomes, FC21 feeder cells, and PM21 particles; and IL-12, IL-15, IL-18, EX21 exosomes, FC21 feeder cells, and PM21 particles.

It is understood and herein contemplated that each step of the disclosed methods of increasing memory NK cell numbers can occur in vitro, in vivo, or ex vivo. That is, the peactivation of NK cells with one or more cytokines can occur in vitro, in vivo, or ex vivo. Similarly, contact of the preactivated NK cells with PM21 particles, EX21 exosomes, and/or FC21 feeder cells can occur in vitro, in vivo, or ex vivo. Also, the resting of the memory NK cells can occur PM21 particles, EX21 exosomes, and/or FC21 feeder cells. Additionally it is understood that whether a step occurs in vitro, ex vivo, or in vivo is entirely independent of the step preceding or subsequent to a particular step. For example, the preactivation can occur in vitro or ex vivo while the contacting of the preactivated NK cells with PM21 particles, EX21 exosomes, and/or FC21 feeder cells occurs in vivo. Alternatively, the preactivation; contact with PM21 particles, EX21 exosomes, and/or FC21 feeder cells; and resting can occur all in vitro or ex vivo. Additionally, the preactivated NK cells can be contacted to PM21 particles, EX21 exosomes, and/or FC21 feeder cells in an allogeneic transplant procedure, a haploidentical transplant procedure or an in vivo immunotherapy procedure. In some aspects, the use of NK-stimulating exosomes in allogeneic transplants, haploidentical transplants or in vivo immunotherapy does not cause graft-versus-host-disease (GVHD).

In one aspect, it is contemplated herein that the disclosed methods can be used with NK cells obtained from any donor source including NK cells obtained from an unselected population of peripheral blood mononuclear cells. In some instances the donor source for the NK cells being used in the disclosed kits for increasing the number of memory NK cells can also be the recipient for the NK cells. Accordingly, the NK cells can be from an autologous source. In other instances the donor source for the NK cells can be a haploidentical or allogeneic donor source. In one aspect, the source of the NK cells can be any source where NK cell progenitor cells may be found including, but not limited to, cord blood or stem cell source such as induced pluripotent stem cells It is understood that a period of rest can benefit the resulting memory NK cells by allowing rapid and vigorous production of IFN-γ when it is re-introduced to a tumor or restimualted by cytokines, at the tumor site. The value of having rapid and vigorous IFN-γ production at the tumor site upon cytokine restimulation or following being introduced to a tumor is three fold: 1) the NK cells don't run out of bullets (both IFN-γ and granzyme); 2) the NK cells last longer in circulation; and 3) the anti-tumor effect with the increased IFN-g is targeted and less general systemic inflammation. Accordingly, and in one aspect, disclosed herein are methods of increasing the number of memory NK cells further comprising resting the memory NK cells following the expansion step b) for 1, 2, 3, 4, 5, 6, 7, 8, 9, 10, 11, 12, 13, 14, 15, 16, 17, 18, 19, 20, or 21 days.

In one aspect, it is appreciated that washing the cells between or after steps can more precisely control exposure to cytokines and/or NK cell effector agent particles or prevent contamination of subsequent steps of the disclosed method or usages of the memory NK cells. Washing can occur in any manner acceptable in the art including, but not limited to, cycles of centrifugation and resuspension in an acceptable wash followed by a final resuspension in media, simple pouring off of culture media followed by one or more rinses with an acceptable media; said washing being conducted at culture temperature, room temperature, or a cold wash (e.g, over ice or in a refrigerated centrifuge). The washes can be accomplished phosphate buffered saline (PBS) or with any appropriate media for culturing NK cells (for example, CELLGRO® GMP media, Roswell Park Memorial Institute (RPMI) institute, Minimal Essential Media (MEM), Eagle's MEM (EMEM), X-VIVO20™, etc.) with or without serum (e.g., fetal bovine serum). Thus, in one aspect, disclosed herein are methods of increasing the number of NK cells comprising a) preactivating NK cells by contacting at least one NK cell with at least one or more stimulatory cytokines; and b) expanding the preactivated NK cells of step a) by contacting said cells with PM21 particles, EX21 exosomes, or FC21 feeder cells; further comprising washing the NK cells after preactivation with IL-12, IL-15, and IL-18 and/or washing the NK cells after expansion with one or more vesicle comprising an NK cell effector agent (i.e., PM21 particles, EX21 exosomes, and/or FC21 feeder cells).

The disclosed methods provide a surprising increase in the number of memory NK cells significantly beyond numbers achieved by alternative methods. As shown in FIG. 1, preactication with stimulatory cytokines followed by expansion of the preactivated cells through contact with PM21 particles expanded NK cell number over 10,000 fold in 15 days. This is a 8-fold increase over expansion with K562-mb21 feeder cells or and 100-fold increase over expansion with PM21 particles alone.

C. Compositions

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular cytokine (for example IL-12, IL-15, or IL-18), PM21 particle, EX21 exosome, or FC21 feeder cell is disclosed and discussed and a number of modifications that can be made to a number of molecules including the cytokine (for example IL-12, IL-15, or IL-18), PM21 particle, EX21 exosome, or FC21 feeder cell are discussed, specifically contemplated is each and every combination and permutation of the cytokine (for example IL-12, IL-15, or IL-18), PM21 particle, EX21 exosome, or FC21 feeder cell and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

The disclosed methods increasing the number of memory NK cells utilize one or more cytokines (for example, IL-12, IL-15, and/or IL-18) in combination with a vesicle comprising an NK cell effector agent, such as, for example, PM21 particles, FC21 feeder cells, and/or EX21 exosomes. It is understood and herein contemplated that it would be advantageous to provide the components utilized in the disclosed methods in a package that would readily allow a person to perform the disclosed methods.

Thus, in one aspect, disclosed herein are kits for increasing the number of memory NK cells comprising one or more cytokines (for example, IL-12, IL-15 and/or IL-18) and one or more vesicle comprising an NK cell effector agent. In one aspect, the vesicle can be PM21 particles, EX21 exosomes, and/or FC21 feeder cells. For example, the disclosed kits can comprise IL-12 and PM21 particles; IL-15 and PM21 particles; IL-18 and PM21 particles; IL-12 and EX21 exosomes, IL-15 and EX21 exosomes; IL-18 and EX21 exosomes; IL-12 and FC21 feeder cells; IL-15 and FC21 feeder cells; IL-18 and FC21 feeder cells; IL-12, IL15, and PM21 particles; IL-12, IL-18, and PM21 particles; IL-15, IL-18, and PM21 particles; IL-12, IL-15, IL-18, and PM21 particles; IL-12, IL15, and EX21 exosomes; IL-12, IL-18, and EX21 exosomes; IL-15, IL-18, and EX21 exosomes; IL-12, IL-15, IL-18, and EX21 exosomes; IL-12, IL15, and FC21 feeder cells; IL-12, IL-18, and FC21 feeder cells; IL-15, IL-18, and FC21 feeder cells; IL-12, IL-15, IL-18, and FC21 feeder cells; IL-12, EX21 exosomes, and PM21 particles; IL-15, EX21 exosomes, and PM21 particles; IL-18, EX21 exosomes, and PM21 particles; IL-12, FC21 feeder cells, and PM21 particles; IL-15, FC21 feeder cells, and PM21 particles; IL-18, FC21 feeder cells, and PM21 particles; IL-12, FC21 feeder cells, and EX21 exosomes; IL-15, FC21 feeder cells, and EX21 exosomes; IL-18, FC21 feeder cells, and EX21 exosomes; IL-12, FC21 feeder cells, PM21 particles, and EX21 exosomes; IL-15, FC21 feeder cells, PM21 particles, and EX21 exosomes; IL-18, FC21 feeder cells, PM21 particles, and EX21 exosomes; IL-12, IL15, EX21 exosomes, and PM21 particles; IL-12, IL-18, EX21 exosomes, and PM21 particles; IL-15, IL-18, EX21 exosomes, and PM21 particles; IL-12, IL-15, IL-18, EX21 exosomes, and PM21 particles; IL-12, IL15, FC21 feeder cells, and PM21 particles; IL-12, IL-18, FC21 feeder cells, and PM21 particles; IL-15, IL-18, FC21 feeder cells, and PM21 particles; IL-12, IL-15, IL-18, FC21 feeder cells, and PM21 particles; IL-12, IL15, EX21 exosomes, and FC21 feeder cells; IL-12, IL-18, EX21 exosomes, and FC21 feeder cells; IL-15, IL-18, EX21 exosomes, and FC21 feeder cells; IL-12, IL-15, IL-18, EX21 exosomes, and FC21 feeder cells; IL-12, EX21 exosomes, FC21 feeder cells, and PM21 particles; IL-15, EX21 exosomes, FC21 feeder cells, and PM21 particles; IL-18, EX21 exosomes, FC21 feeder cells, and PM21 particles; IL-12, IL15, EX21 exosomes, FC21 feeder cells, and PM21 particles; IL-12, IL-18, EX21 exosomes, FC21 feeder cells, and PM21 particles; IL-15, IL-18, EX21 exosomes, FC21 feeder cells, and PM21 particles; or IL-12, IL-15, IL-18, EX21 exosomes, FC21 feeder cells, and PM21 particles.

It is understood and herein contemplated that the NK cell effector agents comprised in the vesicles (e.g., PM21 particles, EX21 exosomes, and/or FC21 feeder cells) can be selected from the group of NK cell effector agents consisting of 4-1BBL, IL-2, IL-21, MICA/B, ULBP2, ICAM-1, 2B4, BCM1/SLAMF2, CD155, CD112, CCR7, DAP12, and DAP10.

It is understood and herein contemplated that the disclosed kits can comprise cytokines in addition to IL-12, IL-15, and/or IL-18. Accordingly, in one aspect are kits for increasing the number of NK cells further comprising 4-1BBL, IL-2, IL-12, IL-18, IL-21, MICA/B, ULBP2, ICAM-1, 2B4, BCM1/SLAMF2, CD155, CD112, CCR7, DAP12, and DAP10.

In one aspect, it is contemplated herein that the disclosed kits can be used with NK cells obtained from a donor source including NK cells obtained from an unselected population of peripheral blood mononuclear cells. In some instances the donor source for the NK cells being used in the disclosed kits for increasing the number of memory NK cells can also be the recipient for the NK cells. Accordingly, the NK cells can be from an autologous source. In other instances the donor source for the NK cells can be a haploidentical or allogeneic donor source.

It is further contemplated herein that there are instances where it would be beneficial to provide NK cells in the kit. Accordingly in one aspect, disclosed herein are kits for increasing the number of memory NK cells further comprising NK cells or an NK cell line.

What is claimed is:

1. A method for increasing the number of memory Natural Killer (NK) cells comprising a) preactivating NK cells by contacting at least one NK cell with at least one or more stimulatory cytokines; and b) expanding the preactivated NK cells of step a) by contacting said cells with plasma membrane (PM) particles with surface bound interleukin (IL)-21 (PM21) particles, exosomes (EX) with surface bound IL-21 (EX21) exosomes, or feeder cells (FC) with surface bound IL-21 (FC21) feeder cells; wherein the NK cells are further contacted with stimulatory peptides 4-1BB ligand (4-1BBL) and IL-21.

2. The method of claim 1, wherein the NK cells are obtained from an unselected population of peripheral blood mononuclear cells.

3. The method of claim 1, wherein the at least one or more stimulatory cytokines is selected from the group consisting of Interleukin-12 (IL-12), Interleukin-15 (IL-15), and Interleukin-18 (IL-18).

4. The method of claim 3, wherein the method comprises contacting the NK cell with 3 stimulatory cytokines.

5. The method of claim 3, further comprising contacting the NK cell with a stimulatory peptide selected from the group consisting of Interleukin-2 (IL-2), Major histocompatibility complex class I-related chain A/B (MICA/B), UL16 Binding Protein 2 (ULBP2), Intracellular adhesion molecule 1 (ICAM-1), 2B4, /signaling lymphocyte activation molecule (SLAM) family member 2 (F2) (BCM1/SLAMF2), cluster of differentiation 155 (CD155), cluster of differentiation 112 (CD112), C-C chemokine receptor type 7 (CCR7), DnaX activation protein of 12 kDa (DAP12), and DnaX activation protein of 10 kDa (DAP10).

6. The method of claim 1, wherein the NK cells are contacted with the IL-12, IL-15, or IL-18 in vitro, in vivo, or ex vivo.

7. The method of claim 1, wherein the NK cells are contacted with the one or more stimulatory cytokines for between about 6 to about 24 hours.

8. The method of claim 1, wherein the PM21 particles, EX21 exosomes, or FC21 feeder cells further comprise one or more stimulatory peptides coupled to a membrane-inserting peptide.

9. The method of claim 8, wherein the membrane-inserting peptide comprises a fused peptide that is capable of membrane insertion, with affinity for a lipid bilayer, and wherein said fused peptide comprises a segment of IG4, cluster of differentiation 4 (CD4), or a combination thereof.

10. The method of claim 8, wherein the one or more stimulatory peptides coupled to a membrane-inserting peptide is a fusion protein encoded by recombinant deoxyribonucleic acid (DNA).

11. The method of claim 8, wherein the membrane-inserting peptide comprises human fragment crystallizable region (Fc), Glycosylphosphatidylinositol (GPI), transmembrane T-cell receptor, or pH low insertion peptide (pHLIP).

12. The method of claim 8, wherein the one or more stimulatory peptides are selected from the group consisting of IL-2, IL-18, IL-21, MICA/B, ULBP2, ICAM-1, 2B4, BCM1/SLAMF2, CD155, CD112, CCR7, DAP12, and DAP10.

13. The method of claim 1, wherein the NK cells are contacted with the PM21 particles, EX21 exosomes, or FC21 feeder cells in vitro, in vivo, or ex vivo.

14. The method of claim 1, wherein the NK cells of step a are contacted with PM21 particles, EX21 exosomes, or FC21 feeder cells for 7, 8, 9, 10, 11, 12, 13, 14, 15, 16, 17, 18, 19, 20, 21, 22, 23, 24, 25, 26, 27, 28, 29, 30, 45, or 60 days.

15. The method of claim 1, further comprising resting the expanded memory NK cells following step b).

16. The method of claim 15, wherein the memory NK cells are rested for at least 1, 2, 3, 4, or 5 days.

17. The method of claim 15, wherein the memory NK cells are rested for no more than 1, 2, 3, 4 or 5 days.

18. The method of claim 1, wherein the PM21 particles, EX21 exosomes, or FC21 feeder cells comprise 4-1BBL and IL-21.

19. The method of claim 18, wherein the 4-1BBL and IL-21 are coupled to a membrane-inserting peptide.

* * * * *